(12) United States Patent
Endou et al.

(10) Patent No.: US 7,244,556 B2
(45) Date of Patent: Jul. 17, 2007

(54) METHOD OF MODULATING A TESTICULAR CARNITINE TRANSPORTER

(75) Inventors: Hitoshi Endou, Sagamihara (JP); Yoshikatsu Kanai, Hachioji (JP); Atsushi Enomoto, Nishio (JP)

(73) Assignee: Human Cell Systems, Inc., Tokyo (JP)

( * ) Notice: Subject to any disclaimer, the term of this patent is extended or adjusted under 35 U.S.C. 154(b) by 207 days.

(21) Appl. No.: 10/479,013

(22) PCT Filed: May 27, 2002

(86) PCT No.: PCT/JP02/05095

§ 371 (c)(1), (2), (4) Date: Nov. 25, 2003

(87) PCT Pub. No.: WO02/097088

PCT Pub. Date: Dec. 5, 2002

(65) Prior Publication Data
US 2005/0054035 A1 Mar. 10, 2005

(30) Foreign Application Priority Data
May 29, 2001 (JP) ............................. 2001-161212

(51) Int. Cl.
G01N 33/53 (2006.01)
C07K 14/435 (2006.01)
(52) U.S. Cl. .......................................... 435/4; 530/350
(58) Field of Classification Search ...................... None
See application file for complete search history.

(56) References Cited

FOREIGN PATENT DOCUMENTS

| EP | 1403368 A1 * | 3/2004 |
|----|--------------|--------|
| WO | WO 00/58473 A2 | 10/2000 |
| WO | WO 01/53453 A2 | 7/2001 |
| WO | WO 01/57190 A2 | 8/2001 |

OTHER PUBLICATIONS

Miyazaki et al. The multispecific organic anion transporter family: properties and pharmacological significance. TRENDS Pharmacol Sci 25(12): 654-662, 2004.*
Pettit et al. The development of site-speicifc drug delivery systems for protein and peptide biopharmaceuticals. Trends in Biotech 16: 343-349, 1998.*
Sekine T, Kusuhara H, Utsunomiya-Tate N, Tsuda M, Sugiyama Y, Kanai Y, Endou H. Molecular cloning and characterization of high-affinity carnitine transporter from rat intestine. Biochem Biophys Res Commun. Oct. 20, 1998; 251(2):586-91.
Cha SH, Sekine T, Kusuhara H, Yu E, Kim JY, Kim DK, Sugiyama Y, Kanai Y, Endou H.Molecular cloning and characterization of multispecific organic anion transporter 4 expressed in the placenta. J Biol Chem. Feb. 11, 2000;275(6):4507-12.
Sekine T, Watanabe N, Hosoyamada M, Kanai Y, Endou H. Expression cloning and characterization of a novel multispecific organic anion transporter. J Biol Chem. Jul. 25, 1997;272(30):18526-9.
Tamai I, Ohashi R, Nezu J, Yabuuchi H, Oku A, Shimane M, Sai Y, Tsuji A Molecular and functional identification of sodium ion-dependent, high affinity human carnitine transporter OCTN2. J Biol Chem. Aug. 7, 1998;273(32);20378-82.

(Continued)

*Primary Examiner*—Bridget Bunner
(74) *Attorney, Agent, or Firm*—Peter F. Corless; Christine C. O'Day; Edwards Angell Palmer & Dodge LLP

(57) ABSTRACT

It is intended to identify and provide a novel carnitine transporter gene participating in carnitine transport in the testis and epididymis and carnitine transporter which is a protein encoded by the gene. A protein comprising the amino acid sequence represented by SEQ ID NO:2 or an amino acid sequence derived therefrom by deletion, substitution or addition of one to several amino acids and being capable of transporting carnitine or its analog; and a gene encoding this protein.

1 Claim, 7 Drawing Sheets

OTHER PUBLICATIONS

Enomoto A, Wempe MF, Tsuchida H, Shin HJ, Cha SH, Anzai N, Goto A, Sakamoto A, Niwa T, Kanai Y, Anders MW, Endou H. Molecular identification of a novel carnitine transporter specific to human testis. Insights into the mechanism of carnitine recognition. J Biol Chem. Sep. 27, 2002:277(39):36262-71. Epub Jun. 27, 2002.

Tamai et al., "Journ. of Biol. Chem.", vol. 275, No. 51, pp. 40064-40072 (2000).

Matalliotakis et al., "Inter. Journ. of Fert. and Wom. Med.", vol. 45, No. 3, pp. 236-240 (2000).

Jeulin et al., "Human Reprod. Update", vol. 2, No. 2, pp. 87-102 (1996).

Wu et al., "Journ. of Pharm. and Experimental Therap.", vol. 290, No. 3, pp. 1482-1492 (1999).

Toshimori et al., "FEBS Letters", vol. 446, No. 2/3, pp. 323-326 (1999).

Tamai et al., "FEBS Letters", vol. 419, No. 1, pp. 107-111 (1997).

Xuan et al., "Biochem. and Biophys. Research Coom.", vol. 306, No. 1, pp. 121-128 (2003).

* cited by examiner

A TESTIS × 100

B TESTIS × 200

C TESTIS×200 (ABSORPTION EXPERIMENT)

D EPIDIDYMIS × 40

E EPIDIDYMIS × 100

F EPIDIDYMIS×100 (ABSORPTION EXPERIMENT)

FIG. 7

EXON-INTRON STRUCTURE OF HUMAN CT2 GENE

| EXON | | | | INTRON | | | EXON | |
|---|---|---|---|---|---|---|---|---|
| No. | SIZE(bp) | 3' COMBINATION | 5' COMBINATION | SIZE(bp) | No. | 3' COMBINATION | 5' COMBINATION | No. |
| 1 | 265 | ...GCAAAGGAG | gtgtttcaaa... | 943 | 1 | ...ttcaaatag | GAGTAGTGA... | 2 |
| 2 | 66 | ...CTCAATGAG | gtaggtggt... | 17914 | 2 | ...ctcttgcag | ATTCCAGAG... | 3 |
| 3 | 118 | ...CCAGGCAAT | gtgagtcag... | 97 | 3 | ...acggtgcag | TTGCAGAAT... | 4 |
| 4 | 266 | ...TTCTGACAG | gtaaaatca... | 9547 | 4 | ...attttttcag | GCTAGGACG... | 5 |
| 5 | 118 | ...CTTGCCATG | gtgagttgt... | 4097 | 5 | ...gtttttttcag | GTTGCAAGT... | 6 |
| 6 | 532 | ...TCCTCCTGG | gtaagtagt... | 3396 | 6 | ...caatgacag | GTGTAGTGG... | 7 |
| 7 | 128 | ...ATCCCCCAG | gtgagttat... | 2759 | 7 | ...tttttttcag | AAACATTAT... | 8 |
| 8 | 110 | ...CATTGTAAG | gtaaggatg... | 4581 | 8 | ...tgtttccag | ATCGCTGGC... | 9 |
| 9 | 100 | ...ATACCACAG | gtgtgcttc... | 6085 | 9 | ...tcctttctag | TTGTTTGTT... | 10 |
| 10 | 337 | ...GTAAGAAAA | | | | | | |

SEQUENCE LISTING

```
<160> NUMBER OF SEQ ID NOS: 2

<210> SEQ ID NO 1
<211> LENGTH: 2048
<212> TYPE: DNA
<213> ORGANISM: Homo sapiens
<220> FEATURE:
<221> NAME/KEY: CDS
<222> LOCATION: (285)..(1916)

<400> SEQUENCE: 1
tcgaggggcc agatctcact cgtagggggt gcctgtgcct ggccgcccgt ttctctaatc      60
cgccgccact tccctagacg gctgctgccc agttctgccc tgcgcctccg tagggcctcc    120
ctctgtgcct ggcaggtgtt ccccagggac aaccgttagt cagagttggt tgccgtttat    180
taaaacctaa tacctgccag gtacactgta cctggcgctt acacatagtt cttcatttga    240
tgttcaccgg gaccctgcaa aggaggagta gtgaaaatgt gtat atg agg act ctg      296
                                                Met Arg Thr Leu
                                                  1 cat gca gtt tct cat cct tac agt aac tca atg aga ttc cag aga gtc      344
His Ala Val Ser His Pro Tyr Ser Asn Ser Met Arg Phe Gln Arg Val
  5                  10                  15                  20 ctc tat ttc ata tgt gcc ttc cag aac atc tct tgt ggt att cac tac      392
Leu Tyr Phe Ile Cys Ala Phe Gln Asn Ile Ser Cys Gly Ile His Tyr
                 25                  30                  35 ttg gct tct gtg ttc atg gga gtc acc cct cat cat gtc tgc agg ccc      440
Leu Ala Ser Val Phe Met Gly Val Thr Pro His His Val Cys Arg Pro
             40                  45                  50 cca ggc aat ttg cag aat ggt gag atc tgg gag ctc tca agg tgt agc      488
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Pro | Gly | Asn | Leu | Gln | Asn | Gly | Glu | Ile | Trp | Glu | Leu | Ser | Arg | Cys | Ser |      |
|     |     | 55  |     |     |     | 60  |     |     |     |     | 65  |     |     |     |     |      |

```
agg aat aag agg gag aac aca tcg agt ttg ggc tat gaa tac act ggc      536
Arg Asn Lys Arg Glu Asn Thr Ser Ser Leu Gly Tyr Glu Tyr Thr Gly
         70                  75                  80 agt aag aaa gag ttt cct tgt gtg gat ggc tac ata tat gac cag aac      584
Ser Lys Lys Glu Phe Pro Cys Val Asp Gly Tyr Ile Tyr Asp Gln Asn
 85                  90                  95                 100 aca tgg aaa agc act gcg gtg acc cag tgg aac ctg gtc tgt gac cga      632
Thr Trp Lys Ser Thr Ala Val Thr Gln Trp Asn Leu Val Cys Asp Arg
                105                 110                 115 aaa tgg ctt gca atg ctg atc cag ccc cta ttt atg ttt gga gtc cta      680
Lys Trp Leu Ala Met Leu Ile Gln Pro Leu Phe Met Phe Gly Val Leu
                    120                 125                 130 ctg gga tcg gtg act ttt ggc tac ttt tct gac agg cta gga cgc cgg      728
Leu Gly Ser Val Thr Phe Gly Tyr Phe Ser Asp Arg Leu Gly Arg Arg
                135                 140                 145 gtg gtc ttg tgg gcc aca agc agt agc atg ttt ttg ttt gga ata gca      776
Val Val Leu Trp Ala Thr Ser Ser Ser Met Phe Leu Phe Gly Ile Ala
            150                 155                 160 gcg gcg ttt gca gtt gat tat tac acc ttc atg gct gct cgc ttt ttt      824
Ala Ala Phe Ala Val Asp Tyr Tyr Thr Phe Met Ala Ala Arg Phe Phe
165                 170                 175                 180 ctt gcc atg gtt gca agt ggc tat ctt gtg gtg ggg ttt gtc tat gtg      872
Leu Ala Met Val Ala Ser Gly Tyr Leu Val Val Gly Phe Val Tyr Val
                    185                 190                 195 atg gaa ttc att ggc atg aag tct cgg aca tgg gcg tct gtc cat ttg      920
Met Glu Phe Ile Gly Met Lys Ser Arg Thr Trp Ala Ser Val His Leu
                200                 205                 210 cat tcc ttt ttt gca gtt gga acc ctg ctg gtg gct ttg aca gga tac      968
His Ser Phe Phe Ala Val Gly Thr Leu Leu Val Ala Leu Thr Gly Tyr
            215                 220                 225 ttg gtc agg acc tgg tgg ctt tac cag atg atc ctc tcc aca gtg act     1016
Leu Val Arg Thr Trp Trp Leu Tyr Gln Met Ile Leu Ser Thr Val Thr
230                 235                 240 gtc ccc ttt atc ctg tgc tgt tgg gtg ctc cca gag aca cct ttt tgg     1064
Val Pro Phe Ile Leu Cys Cys Trp Val Leu Pro Glu Thr Pro Phe Trp
245                 250                 255                 260 ctt ctc tca gag gga cga tat gaa gaa gca caa aaa ata gtt gac atc     1112
Leu Leu Ser Glu Gly Arg Tyr Glu Glu Ala Gln Lys Ile Val Asp Ile
                265                 270                 275 atg gcc aag tgg aac agg gca agc tcc tgt aaa ctg tca gaa ctt tta     1160
Met Ala Lys Trp Asn Arg Ala Ser Ser Cys Lys Leu Ser Glu Leu Leu
                280                 285                 290 tca ctg gac cta caa ggt cct gtt agt aat agc ccc act gaa gtt cag     1208
Ser Leu Asp Leu Gln Gly Pro Val Ser Asn Ser Pro Thr Glu Val Gln
            295                 300                 305 aag cac aac cta tca tat ctg ttt tat aac tgg agc att acg aaa agg     1256
Lys His Asn Leu Ser Tyr Leu Phe Tyr Asn Trp Ser Ile Thr Lys Arg
            310                 315                 320 aca ctt acc gtt tgg cta atc tgg ttc act gga agt ttg gga ttc tac     1304
Thr Leu Thr Val Trp Leu Ile Trp Phe Thr Gly Ser Leu Gly Phe Tyr
325                 330                 335                 340 tcg ttt tcc ttg aat tct gtt aac tta gga ggc aat gaa tac tta aac     1352
Ser Phe Ser Leu Asn Ser Val Asn Leu Gly Gly Asn Glu Tyr Leu Asn
                345                 350                 355 ctc ttc ctc ctg ggt gta gtg gaa att ccc gcc tac acc ttc gtg tgc     1400
Leu Phe Leu Leu Gly Val Val Glu Ile Pro Ala Tyr Thr Phe Val Cys
            360                 365                 370
```

-continued

```
atc gcc atg gac aag gtc ggg agg aga aca gtc ctg gcc tac tct ctt    1448
Ile Ala Met Asp Lys Val Gly Arg Arg Thr Val Leu Ala Tyr Ser Leu
        375                 380                 385 ttc tgc agt gca ctg gcc tgt ggt gtc gtt atg gtg atc ccc cag aaa    1496
Phe Cys Ser Ala Leu Ala Cys Gly Val Val Met Val Ile Pro Gln Lys
    390                 395                 400 cat tat att ttg ggt gtg gta aca gct atg gtt gga aaa ttt gcc atc    1544
His Tyr Ile Leu Gly Val Val Thr Ala Met Val Gly Lys Phe Ala Ile
405                 410                 415                 420 ggg gca gca ttt ggc ctc att tat ctt tat aca gct gag ctg tat cca    1592
Gly Ala Ala Phe Gly Leu Ile Tyr Leu Tyr Thr Ala Glu Leu Tyr Pro
                425                 430                 435 acc att gta aga tcg ctg gct gtg gga agc ggc agc atg gtg tgt cgc    1640
Thr Ile Val Arg Ser Leu Ala Val Gly Ser Gly Ser Met Val Cys Arg
            440                 445                 450 ctg gcc agc atc ctg gcg ccg ttc tct gtg gac ctc agc agc att tgg    1688
Leu Ala Ser Ile Leu Ala Pro Phe Ser Val Asp Leu Ser Ser Ile Trp
        455                 460                 465 atc ttc ata cca cag ttg ttt gtt ggg act atg gcc ctc ctg agt gga    1736
Ile Phe Ile Pro Gln Leu Phe Val Gly Thr Met Ala Leu Leu Ser Gly
    470                 475                 480 gtg tta aca cta aag ctt cca gaa acc ctt ggg aaa cgg cta gca act    1784
Val Leu Thr Leu Lys Leu Pro Glu Thr Leu Gly Lys Arg Leu Ala Thr
485                 490                 495                 500 act tgg gag gag gct gca aaa ctg gag tca gag aat gaa agc aag tca    1832
Thr Trp Glu Glu Ala Ala Lys Leu Glu Ser Glu Asn Glu Ser Lys Ser
                505                 510                 515 agc aaa tta ctt ctc aca act aat aat agt ggg ctg gaa aaa acg gaa    1880
Ser Lys Leu Leu Leu Thr Thr Asn Asn Ser Gly Leu Glu Lys Thr Glu
            520                 525                 530 gcg att acc ccc agg gat tct ggt ctt ggt gaa taa atgtgccatg         1926
Ala Ile Thr Pro Arg Asp Ser Gly Leu Gly Glu
        535                 540 cctgctgtct agcacctgaa atattattta ccctaatgcc tttgtattag aggaatctta    1986
ttctcatctc ccatatgttg tttgtatgtc tttttaataa attttgtaag aaaaaaaaaa    2046
aa                                                                  2048

<210> SEQ ID NO 2
<211> LENGTH: 543
<212> TYPE: PRT
<213> ORGANISM: Homo sapiens

<400> SEQUENCE: 2

Met Arg Thr Leu His Ala Val Ser His Pro Tyr Ser Asn Ser Met Arg
 1               5                  10                  15

Phe Gln Arg Val Leu Tyr Phe Ile Cys Ala Phe Gln Asn Ile Ser Cys
            20                  25                  30

Gly Ile His Tyr Leu Ala Ser Val Phe Met Gly Val Thr Pro His His
        35                  40                  45

Val Cys Arg Pro Pro Gly Asn Leu Gln Asn Gly Glu Ile Trp Glu Leu
    50                  55                  60

Ser Arg Cys Ser Arg Asn Lys Arg Glu Asn Thr Ser Ser Leu Gly Tyr
65                  70                  75                  80

Glu Tyr Thr Gly Ser Lys Lys Glu Phe Pro Cys Val Asp Gly Tyr Ile
                85                  90                  95

Tyr Asp Gln Asn Thr Trp Lys Ser Thr Ala Val Thr Gln Trp Asn Leu
            100                 105                 110
```

-continued

```
Val Cys Asp Arg Lys Trp Leu Ala Met Leu Ile Gln Pro Leu Phe Met
        115                 120                 125

Phe Gly Val Leu Leu Gly Ser Val Thr Phe Gly Tyr Phe Ser Asp Arg
130                 135                 140

Leu Gly Arg Arg Val Val Leu Trp Ala Thr Ser Ser Ser Met Phe Leu
145                 150                 155                 160

Phe Gly Ile Ala Ala Ala Phe Ala Val Asp Tyr Tyr Thr Phe Met Ala
                165                 170                 175

Ala Arg Phe Phe Leu Ala Met Val Ala Ser Gly Tyr Leu Val Val Gly
                180                 185                 190

Phe Val Tyr Val Met Glu Phe Ile Gly Met Lys Ser Arg Thr Trp Ala
                195                 200                 205

Ser Val His Leu His Ser Phe Ala Val Gly Thr Leu Leu Val Ala
                210                 215                 220

Leu Thr Gly Tyr Leu Val Arg Thr Trp Trp Leu Tyr Gln Met Ile Leu
225                 230                 235                 240

Ser Thr Val Thr Val Pro Phe Ile Leu Cys Cys Trp Val Leu Pro Glu
                245                 250                 255

Thr Pro Phe Trp Leu Leu Ser Glu Gly Arg Tyr Glu Glu Ala Gln Lys
                260                 265                 270

Ile Val Asp Ile Met Ala Lys Trp Asn Arg Ala Ser Ser Cys Lys Leu
                275                 280                 285

Ser Glu Leu Leu Ser Leu Asp Leu Gln Gly Pro Val Ser Asn Ser Pro
290                 295                 300

Thr Glu Val Gln Lys His Asn Leu Ser Tyr Leu Phe Tyr Asn Trp Ser
305                 310                 315                 320

Ile Thr Lys Arg Thr Leu Thr Val Trp Leu Ile Trp Phe Thr Gly Ser
                325                 330                 335

Leu Gly Phe Tyr Ser Phe Ser Leu Asn Ser Val Asn Leu Gly Gly Asn
                340                 345                 350

Glu Tyr Leu Asn Leu Phe Leu Leu Gly Val Val Glu Ile Pro Ala Tyr
                355                 360                 365

Thr Phe Val Cys Ile Ala Met Asp Lys Val Gly Arg Arg Thr Val Leu
        370                 375                 380

Ala Tyr Ser Leu Phe Cys Ser Ala Leu Ala Cys Gly Val Val Met Val
385                 390                 395                 400

Ile Pro Gln Lys His Tyr Ile Leu Gly Val Val Thr Ala Met Val Gly
                405                 410                 415

Lys Phe Ala Ile Gly Ala Ala Phe Gly Leu Ile Tyr Leu Tyr Thr Ala
                420                 425                 430

Glu Leu Tyr Pro Thr Ile Val Arg Ser Leu Ala Val Gly Ser Gly Ser
                435                 440                 445

Met Val Cys Arg Leu Ala Ser Ile Leu Ala Pro Phe Ser Val Asp Leu
        450                 455                 460

Ser Ser Ile Trp Ile Phe Ile Pro Gln Leu Phe Val Gly Thr Met Ala
465                 470                 475                 480

Leu Leu Ser Gly Val Leu Thr Leu Lys Leu Pro Glu Thr Leu Gly Lys
                485                 490                 495

Arg Leu Ala Thr Thr Trp Glu Glu Ala Ala Lys Leu Glu Ser Glu Asn
                500                 505                 510
```

-continued

```
Glu Ser Lys Ser Ser Lys Leu Leu Leu Thr Thr Asn Asn Ser Gly Leu
        515                 520                 525

Glu Lys Thr Glu Ala Ile Thr Pro Arg Asp Ser Gly Leu Gly Glu
        530                 535                 540
```

…

METHOD OF MODULATING A TESTICULAR CARNITINE TRANSPORTER

TECHNICAL FIELD

The present invention relates to a gene participating in sodium dependent transport of carnitine and its analog in the testis and the epididymis and a polypeptide encoded by the gene.

BACKGROUND ART

Carnitine has an important function in beta-oxidation of fatty acids in every organ of a living body. Cells in every organ produce ATP (adenosine triphosphate), which is the energy source for the cells, in mitochondria owing to the beta-oxidation of fatty acids. An acyl group of the fatty acids is transported in the mitochondria through a carnitine action to be transformed into acyl Co-A, and then the acyl Co-A is beta-oxidized to generate ATP. Many carnitines are diet-induced, and, though a part thereof is biosynthesized in the liver and the brain, almost all the cells need to uptake carnitines from outside; therefore, it has been assumed that a carnitine-specific transporter exists in the cell membrane according to past physiological studies.

Studies have been conducted on the carnitine uptake by various cells by the use of experiment systems employing the removed organ perfusion method or the isolated cell membrane vesicular system. However, it has been difficult to analyze the system of carnitine transport through cell membrane in detail by the conventional methods, and there has been a demand for isolation and analysis of the transporter itself.

The rat CT1 (Sekine, T. et al., *Biochem. Biophis. Res. Commun.*, Vol. 251, pp. 586-591, 1998) has been isolated as the carnitine transporter. The hOCTN2 (Tamai, I. et al., *J. Biol. Chem.*, Vol. 273, pp. 20378-20382, 1998) has been reported to be a human homologous gene of the CT1. The carnitine transporters are widely distributed in organs of the whole body to contribute to the carnitine uptake by various cells. They exist also in the kidney to carry out a function of reabsorption of carnitine from the renal tubules.

According to the past studies, it has been clarified that a carnitine concentration in the testis and the epididymis is the highest in the living body and reached the 2,000 times of the serum level depending on the specie of the carnitine. Since the duct of epididymis is an organ governing nutrition and maturity of sperms, the relationship between carnitine and sperm function has attracted attention.

It has been clarified that the sperms produced in the testis are premature and low in motility and lacks in fertilizability at that stage. The sperms leaving the testis move to the epididymis and subjected to various modifications therein and matured. Further, flagellar movement is necessary for the sperm fertility, which requires enormous energy. It is reasonable to consider that a large amount of carnitine is required for the production of ATP which is the energy source for the flagellar movement.

Actually, a study revealing a positive relationship between the carnitine concentration in the human semen and the number and motility of sperms has been reported. Also, in the clinical medicine, it has been reported that carnitine administration had resulted in an increase in fertilization probability of idiopathic infertility patients.

Thus, the carnitine transport specific to the testis and the epididymis has been considered to have an important function in the maturity and the fertilizability of sperms and has been studied by the experiment systems employing the removed organ perfusion method or the isolated cell membrane vesicular system. Though the existence of an active carnitine transport system has been clarified from the studies, its molecular substance has been indefinite.

Organic anion transporters OAT1 (organic anion transporter 1) (Sekine, T. et al., *J. Biol. Chem.*, Vol. 272, pp. 18526-18529, 1997), OAT2 (Sekine, T., *FEBS letter*, Vol. 429, pp. 179-182, 1998), OAT3 (Kusuhara, H. et al., *J. Biol. Chem.*, Vol. 274, pp. 13675-13680, 1999), and OAT4 (Cha, S. H. et al., *J. Biol. Chem.*, Vol. 275, pp. 4507-4512, 2000), which have the central role in drug transport in the kidney, liver, brain, and placenta, have been isolated and reported by some of the inventors of the present invention. These transporters belonging to an OAT family are transporters that can transport many different organic anions in chemical structure and also transport of various anionic drugs.

Recently, an OCT (organic cation transporter) family which recognizes organic cations also has recently been identified. Since carnitine is an organic ion having both of a positive charge and a negative charge, it is assumed that the carnitine transporter is positioned between the OAT family and the OCT family from the point of molecular evolution.

In view of these facts, the present inventors have presumed that the carnitine transporter specific to the testis and the epididymis belongs to the organic ion transporter family.

DISCLOSURE OF THE INVENTION

An object of the present invention is to identify and provide a novel carnitine transporter gene participating in carnitine transport in the testis and the epididymis and a carnitine transporter which is a polypeptide encoded by the gene.

BRIEF DESCRIPTION OF THE DRAWINGS

FIGS. 6A-6C are photos of testis and FIGS. 6D-6E are photos of epididymis; FIGS. 6A and 6D show testis and epididymis, respectively, which were incubated with polyclonal anti-CT2 antibody and then reacted with anti-rabbit IgG antibody labeled with peroxidase and stained by diaminobenzidine; FIGS. 6B and 6E are amplified pictures of FIGS. 6A and 6D, respectively. FIGS. 6C and 6F show testis and epididymis, respectively, which were incubated with polyclonal anti-CT2 antibody and then reacted with anti-rabbit IgG antibody labeled with peroxidase and stained by diaminobenzidine.

FIG. 7 shows a result of analyzing a structure of a human genome of CT2 gene.

BEST MODE FOR CARRYING OUT THE INVENTION

Figure 1:
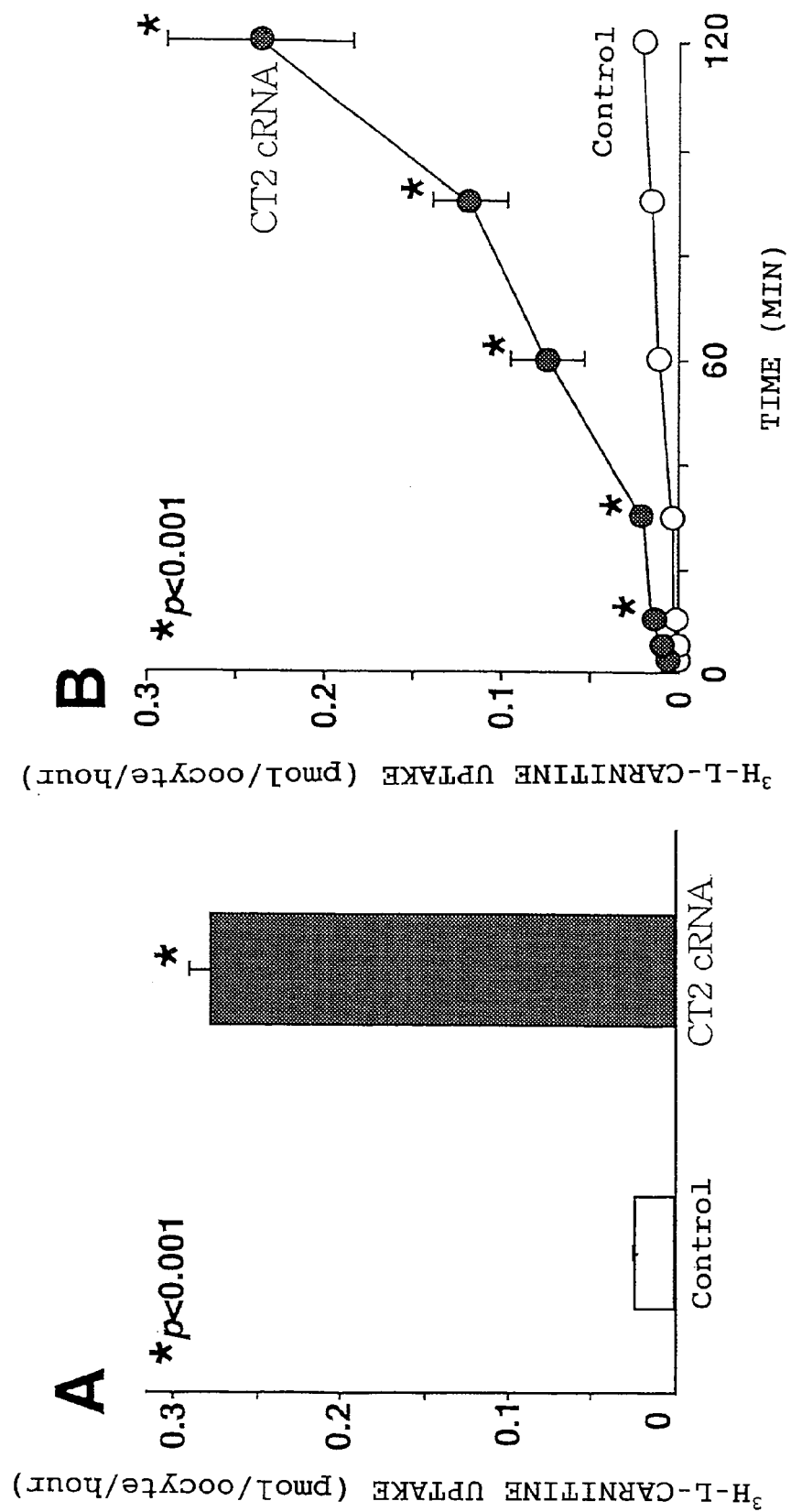
FIG. 1 shows (A) a result and (B) a time dependence of an experiment on carnitine uptake by oocytes into which a cRNA of human CT2 gene was injected.

The present invention relates to (1) a protein having an ability to transport carnitine or its analog, comprising an amino acid sequence represented by SEQ ID NO: 2 or an amino acid sequence derived from the said amino acid sequence by deletion, substitution, or addition of one to several amino acids.

Also, the present invention relates to (2) a gene encoding the above-described protein.

Further, the invention relates to (3) a gene comprising a DNA having a base sequence represented by SEQ ID NO. 1 or a DNA encoding a protein which hybridizes with the said DNA under stringent conditions and has an ability to transport carnitine and its analog in a sodium dependent manner.

Still further, the invention relates to (4) an expression vector having the above-described gene or a gene encoding a protein of the said gene.

Also, the invention relates to (5) a host cell transformed by the above-described expression vector.

Further, the invention relates to (6) a nucleotide including a partial sequence of consecutive 14 or more bases of the base sequence represented by SEQ ID NO. 1 or a complementary sequence thereof.

Still further, the invention relates to (7) a probe comprising the above-described nucleotide and detecting the gene encoding a protein having an ability to transport carnitine and its analog in a sodium dependent manner.

Also, the invention relates to (8) a method of modulating an expression of the gene encoding a protein having an ability to transport carnitine and its analog in a sodium dependent manner by using the above-described nucleotide.

Further, the invention relates to (9) an antibody to the protein defined in (1).

Still further, the invention relates to (10) a method of detecting a function of subjected materials as a substrate to the ability of the protein of transporting carnitine and its analog in a sodium dependent manner, by using the protein defined in (1).

Also, the invention relates to (11) a method of adjusting kinetics of carnitine and its analog transported by the protein defined in (1) in the testis and the epididymis, by modulating the ability of the said protein of transporting carnitine and its analog, by using the protein, its specific antibody, its promoter, or its inhibitor.

Further, the invention relates to (12) a method of adjusting an influence of carnitine and its analog transported by the protein defined in (1) on spermatids, by modulating the ability of the said protein of transporting carnitine and its analog, by using the said protein, its specific antibody, its promoter, or its inhibitor.

Still further, the invention relates to (13) a method of adjusting an influence of carnitine and its analog transported by the protein defined in (1) on a fertilizability of spermatids, by modulating the ability of the said protein of transporting carnitine and its analog, by using the protein, its specific antibody, its promoter, or its inhibitor.

Also, the invention relates to (14) a method of detecting and adjusting an influence of carnitine and its analog transported by the protein defined in (1) on a fertilizability of spermatids or fertilizability of an individual, by making the protein express in an excessive amount in a specific cell or modulating the ability of the said protein existing in the cell of transporting carnitine and its analog, by using the said protein, its specific antibody, its promoter, or its inhibitor.

Namely, the inventors have isolated the four organic anion transporters OAT1, OAT2, OAT3, and OAT4 as described above. Amino acid sequences of these organic anion transporters are about 40% homologous with each other. The inventors have investigated EST (expressed sequence tag) database based on these sequences to identify a novel cDNA fragment which is homologous with OAT1, OAT2, OAT3 and OAT4. Using the cDNA fragment, the inventors have identified a novel clone (CT2) which had not been reported according to the human testis cDNA library to accomplish the present invention.

The carnitine transporter CT2 of the present invention comprises an ability of transporting L-carnitine and its analog from one cell to another through a cell membrane, and a narrow substrate selectivity comparing other drug transporters belonging to the OAT family or the OCT family.

The protein of the present invention includes a protein having the amino acid sequence represented by SEQ ID NO: 2 and a protein having the amino acid sequence derived from the said amino acid sequence by deletion, substitution, or addition of one to several amino acids. An amount of the deletion, the substitution, or the addition of the amino acid(s) may be to such an extent that organic anion transport activity is not lost, and the number of the amino acids may generally be from 1 to about 110, preferably from 1 to about 55. Amino acid sequence of each of these proteins has a homology to the amino acid sequence represented by SEQ ID NO: 2 of generally 75%, preferably 90%.

The gene of the present invention includes a gene comprising a DNA having a base sequence represented by SEQ ID NO. 1 and a gene comprising a DNA encoding a protein which hybridizes with the DNA having the base sequence represented by SEQ ID NO. 1 under stringent conditions and has an ability to transport carnitine and its analog in a sodium dependent manner.

The hybridization under stringent conditions of the present invention may be conducted in a hybridization solution of 5×SSC (standard saline citrate) or a hybridization solution having a salt concentration equivalent to 5×SSC under a temperature condition of from 37° C. to 42° C. for about 12 hours and then preliminarily washed with a solution of 5×SSC, or a solution having a salt concentration equivalent to 5×SSC, followed by washing with a solution of 1×SSC or a solution having a salt concentration equivalent to 1×SSC. The higher stringency can be achieved by conducting the washing with a solution of 0.1×SSC or a solution having a salt concentration equivalent to 0.1×SSC.

The carnitine transporter gene and the protein of the present invention can be isolated and obtained by screening using an organ, a tissue, or a cultured cell of a suitable mammal as a gene source. The mammal includes non-human animals; such as a dog, a cow, a horse, a goat, a sheep, a monkey, a pig, a rabbit, a rat, and a mouse; and a human.

The screening and isolation of the gene may preferably be conducted by a homology screening, a PCR screening or the like.

The base sequence of the obtained cDNA may be determined by an ordinary method to analyze a translation region, whereby determining an amino acid sequence of a protein, CT2, encoded by the base sequence.

It is possible to verify that the obtained cDNA is the cDNA of a carnitine transporter, namely, the gene product encoded in the cDNA is a carnitine transporter, by the following manner, for example.

It is possible to confirm the ability to transport (uptake) carnitine into a cell by expressing a cRNA prepared from the obtained CT2cDNA by introducing the cRNA into an oocyte and measuring a substrate uptake into the cell employing an ordinary uptake experiment (Sekine, T. et al., *Biochem. Biophis. Res. Commun.*, Vol. 251, pp. 586-591, 1998) wherein carnitine is used as a substrate.

Also, it is possible to investigate a transport characteristic and a substrate specificity of the CT2 by applying a similar uptake experiment to the expressed cell.

Further, it is possible to investigate characteristics of the CT2 such as a time dependent transport, a sodium dependence, a substrate selectivity, and a pH dependence by applying a similar uptake experiment to the expressed cell.

By screening a suitable cDNA library or a genomic DNA library prepared from a different gene source using the obtained cDNA of the CT2 gene, it is possible to isolate a homologous gene, a chromogene, or the like, derived from a different tissue or a different organism.

Also, by using a synthetic primer designed based on disclosed information of the base sequence of the gene of the present invention (represented by SEQ ID NO. 1 or a part thereof), it is possible to isolate the gene from the cDNA library according to an ordinary PCR method.

DNA libraries such as the cDNA library and the genomic DNA library can be prepared by the method. For example, described in *Molecular Cloning*; written by Sambrook, J, Fritsh, E. F. and Maniatis, T.; published by Cold Spring Harbor Laboratory Press in 1989. Alternatively, a commercially available library may be used when it is purchasable.

In order to obtain a human genomic structure of the CT2 gene, the genomic DNA library is screened using the cDNA of the obtained CT2 gene to analyze the clone obtained by the screening. Alternatively, it may be searched using a homology search program on the basis of publicly disclosed information of human genome analysis results.

The carnitine transporter (CT2) of the present invention can be produced by a gene recombinant technology using, for example, the cDNA encoding the carnitine transporter. For instance, the DNA (such as cDNA) encoding the carnitine transporter is incorporated into a suitable expression vector, such as a plasmid vector, a phage vector, and a virus vector to introduce the obtained recombinant DNA into a suitable host cell. An expression system (host vector system) for producing a polypeptide includes expression systems of bacteria, yeast, an insect cell, and a mammal cell. Among the above expression systems, it is desirable to use the insect cell and the mammal cell for the purpose of obtaining a functional protein.

For example, when expressing the polypeptide in the mammal, the DNA encoding the carnitine transporter is inserted downstream of a suitable promoter (such as SV40 promoter, LTR promoter, and elongation 1 α promoter) in a suitable expression vector (such as a plasmid vector, a retrovirus-based vector, a papillomavirus vector, a vacciniavirus vector, and a SV40-based vector) to construct the expression vector. Then, a suitable animal cell is transformed by the obtained expression vector, and the transformant is cultured in a proper medium to produce the desired polypeptide. The host mammal cells includes a monkey COS-7 cell, a Chinese hamster CHO cell, a human Hela cell or a cell strain of a primary culture cell derived from the kidney tissue, a pig kidney-derived LLC-PK1 cell, an opossum kidney-derived OK cell, mouse-derived proximal convoluted tubules S1, S2, and S3 cells, and the like.

Examples of the cDNA encoding the carnitine transporter CT2 includes, but not limited to, the cDNA having the base sequence represented by SEQ ID NO. 1, and, also, a DNA corresponding to the amino acid sequence and encoding the polypeptide may be used as the cDNA. In this case, it is known that one amino acid is encoded by 1 to 6 kinds of codons, and the codon(s) to be used may be selected arbitrarily, but, it is desirable to design a sequence which enables a higher level of expression in view of frequency of using codon of the host used for the expression. The DNA having the designed base sequence is obtainable by a DNA chemical synthesis, a combination with a fragment of the above-described cDNA, a partial alteration of the base sequence, or the like. Artificial partial alteration and mutation introduction of the base sequence can be carried out by the site specific mutagenesis disclosed in Mark, D. F. et al., *Proc. Natl. Acad. Sci. USA*, Vol. 18, pp. 5662-5666, 1984, using a primer constituted of synthetic oligonucleotides encoding the desired alteration.

The nucleotide (oligonucleotide or polynucleotide) which hybridizes with the carnitine transporter gene of the present invention under stringent conditions can be used as the probe for detecting the carnitine transporter gene and also as an antisense oligonucleotide, a ribozyme, or a decoy for modulating the carnitine transporter expression. The nucleotide includes a nucleotide comprising a partial sequence of consecutive 14 or more bases of the base sequence represented by SEQ ID NO. 1 or a complementary sequence thereof, and, the longer sequence such as that including 20 or more bases and 30 or more bases may be used as the partial sequence in order to enhance specificity of the hybridization.

Further, by using the carnitine transporter of the present invention or its immunologically equivalent polypeptide, it is possible to obtain an antibody thereof, and the antibody can be used for carnitine transporter detection and purification. The antibody can be produced by using the carnitine transporter of the present invention, a synthetic peptide having a fragment or a partial sequence of the carnitine transporter, as an antigen. A polyclonal antibody can be produced by an ordinary method of inoculating the antibody to a host animal (such as a rat and a rabbit) and recovering an antiserum, and a monoclonal antibody can be produced by an ordinary hybridoma method or the like.

By using the protein of the present invention, it is possible to detect function of subjected materials as a substrate to the ability of the said protein transporting carnitine and its analog in a sodium dependent manner.

Further, by modulating the ability of the protein of the present invention of transporting carnitine and its analog using the protein, its specific antibody, its promoter (for example hormones such as an androgen), or its inhibitor (such as an antisense nucleotide), it is possible to adjust kinetics of carnitine and its analog transported by the said protein in the testis and the epididymis.

Furthermore, by modulating the ability of the protein of the present invention of transporting carnitine and its analog using the protein, its specific antibody, its promoter (for example hormones such as an androgen), or its inhibitor (such as an antisense nucleotide), it is possible to adjust an influence on fertilizability of the spermatids of carnitine and its analog transported by the said protein.

Still further, by modulating the ability of the protein of the present invention of transporting carnitine and its analog using the protein, its specific antibody, its promoter (for example hormones such as an androgen), or its inhibitor (such as an antisense nucleotide), it is possible to adjust an influences on fertilizability of the spermatids or an individual of carnitine and its analog transported by the said protein.

In addition, by making the protein of the present invention express in an excessive amount in a particular cell, or by modulating the ability of the said protein already existing in a cell of transporting carnitine and its analog using the protein, its specific antibody, its promoter (for example hormones such as an androgen), or its inhibitor (such as an antisense nucleotide), it is possible to detect or adjust an influence on the fertilizability of spermatids or an individual by carnitine and its analog transported by the said protein.

EXAMPLES

The present invention will hereinafter be described in more detail by examples, but it is not limited to these examples at all.

Note that operations in the following examples are performed in accordance with the method described in *Molecular Cloning*: written by Sambrook, J., Fritsh, E. F., and Maniatis, T.; published by Cold Spring Harbor Laboratory Press in 1989 or, when using a commercially available kit, in accordance with instructions thereof unless otherwise noted.

Example 1

Isolation and Analysis of Carnitine Transporter (CT2) cDNA Specific to Testis and Epididymis Based on base sequence information of OAT1, OAT2, OAT3, OAT4, and CT1, which were isolated by some of the inventors, publicly disclosed EST database was searched. As a result of this search, a novel cDNA fragment AA778598 which is homologous with OAT1, OAT2, OAT3, OAT4, and CT1 was obtained.

By using a probe labeled AA778598 with $^{32}$P, a human testis cDNA library prepared in advance was screened. Hybridization was conducted in a hybridization solution at 50° C. all day and night, and then a filter film was washed with 0.1×SSC (standard saline citrate)/0.1% SDS (sodium dodecyl sulfate) at 50° C. Used as the hybridization solution was a buffer solution of pH 6.5 containing 50% formamide, 5×SSC, 3×Denhard solution, 0.2% SDS, 10% dextran sulfate, 0.2 mg/ml denatured sermon sperm DNA, 2.5 mM sodium pyrophosphate, 25 mM MES, and 0.01% Antifoam B (foam inhibitor; a product of Sigma-Aldrich, Co.). A clone isolated in λZipLox was subcloned to a plasmid vector pZL1 by an in vitro excision method. As a result, a novel cDNA (CT2cDNA) having carnitine transport activity was obtained.

Determination of a base sequence of the cDNA (CT2cDNA) obtained by the above operation was performed by an automatic sequencer (product of Applied Biosystems) using a specific primer (see SEQ ID NO.1).

Next, a cRNA (RNA complementary to cDNA) was prepared in vitro from a plasmid containing the CT2cDNA by using a T7RNA polymerase (see Sekine, T., et al., *J. Biol. Chem.*, Vol. 272, pp. 18526-18529, 1997).

The thus-obtained cRNA was injected into oocytes of a platanna in accordance with the already reported method (Sekine, T., et al., *J. Biol. Chem.*, Vol. 272, pp. 18526-18529, 1997), and an uptake experiment by radioactive labeled L-carnitine was conducted on the oocytes. As a result, it was proved that the oocytes which expressed the CT2 exhibit $^3$H-L-carnitine uptake as shown in FIG. 1A. In contrast, uptake of $^{14}$C-PAH (paraamino hippuric acid) which is a representative organic anion and uptake of $^{14}$C-TEA (tetraethyl ammonium) which is an organic cation were not observed.

Hereinafter, results of a transport function analysis, a study on substrate selectivity, an analysis of gene expression, an immunological study on the protein encoded by the gene in the testis and the epididymis, and a structure analysis of the CT2 gene in a human genome, all of which were conducted using the CT2 of the present invention, will be described in order.

(1) An experiment on time dependence of the carnitine transport by CT2 was conducted.

As a result of the experiment, the oocytes which expressed the CT2 exhibited time dependence of $^3$H-L-carnitine uptake as shown in FIG. 1B. From this result, it was proved that the CT2 not only combines with carnitine but also serves as a transporter transporting carnitine in cells.

(2) A Michaelis-Menten kinetics experiment on the carnitine transport by CT2 was conducted.

A concentration dependence of the carnitine transport by CT2 was studied through an investigation of changes in amounts of uptake of various concentration carnitines by CT2. The uptake experiment of radioactive labeled carnitines was performed by using oocytes into which the CT2cRNA was injected and in accordance with the above-described method. As a result (FIG. 2A), a Km value of the L-carnitine uptake was about 20.3 μM.

(3) An influence to be exerted by D-carnitine, which is an isomer of L-carnitine, on the L-carnitine transport by CT2 was studied.

Figure 2:
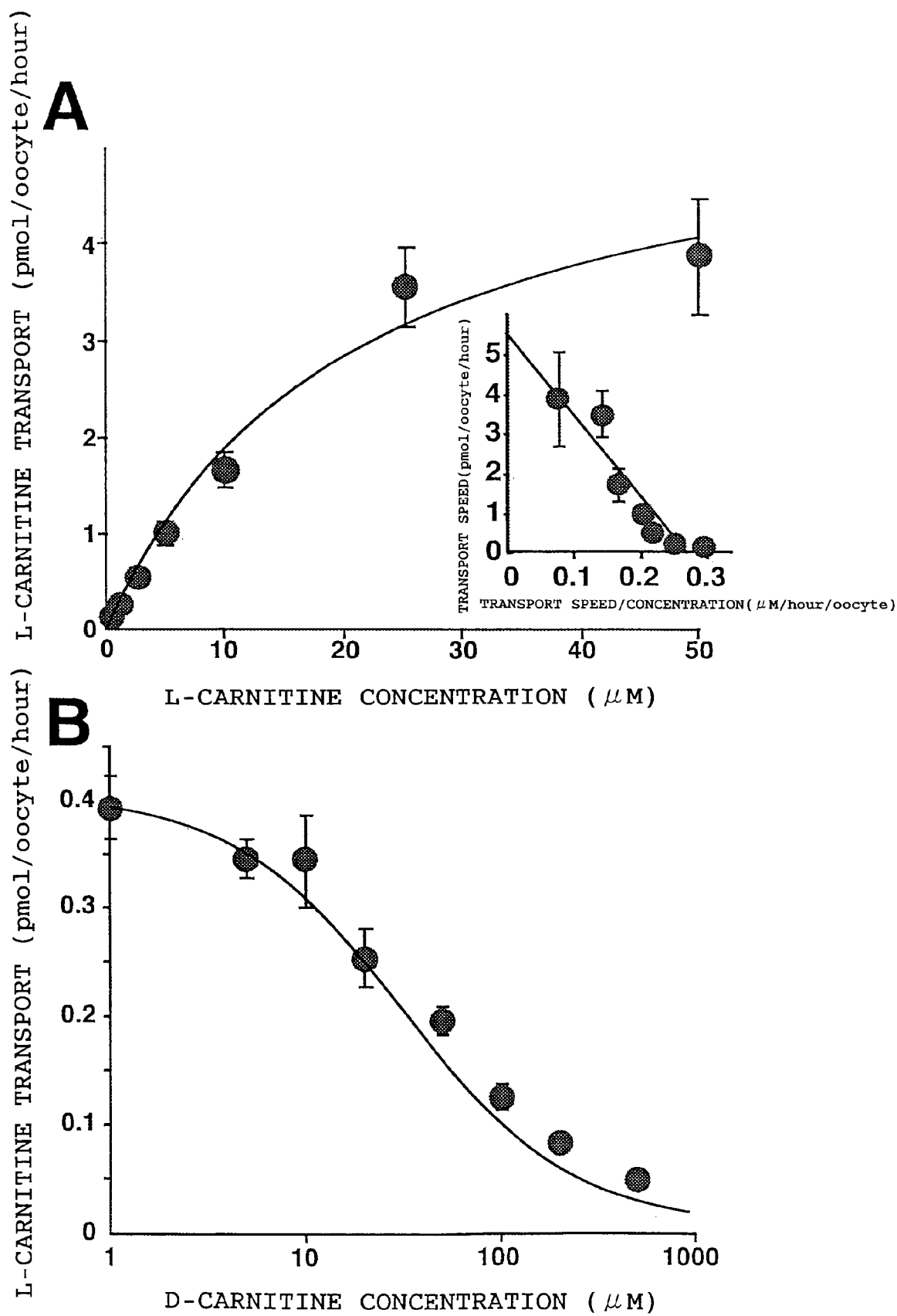
FIG. 2 shows (A) a result of a Michaelis-Menten kinetics experiment on carnitine uptake by oocytes into which the cRNA of human CT2 gene was injected and (B) a result of D-carnitine inhibition effect in L-carnitine transport by the CT2.

As shown in FIG. 2B, D-carnitine inhibited the L-carnitine transport by CT2 in a concentration dependent manner. A Ki value was about 30.1 μM.

(4) A sodium dependence of the CT2 in the carnitine transport was studied.

Figure 3:
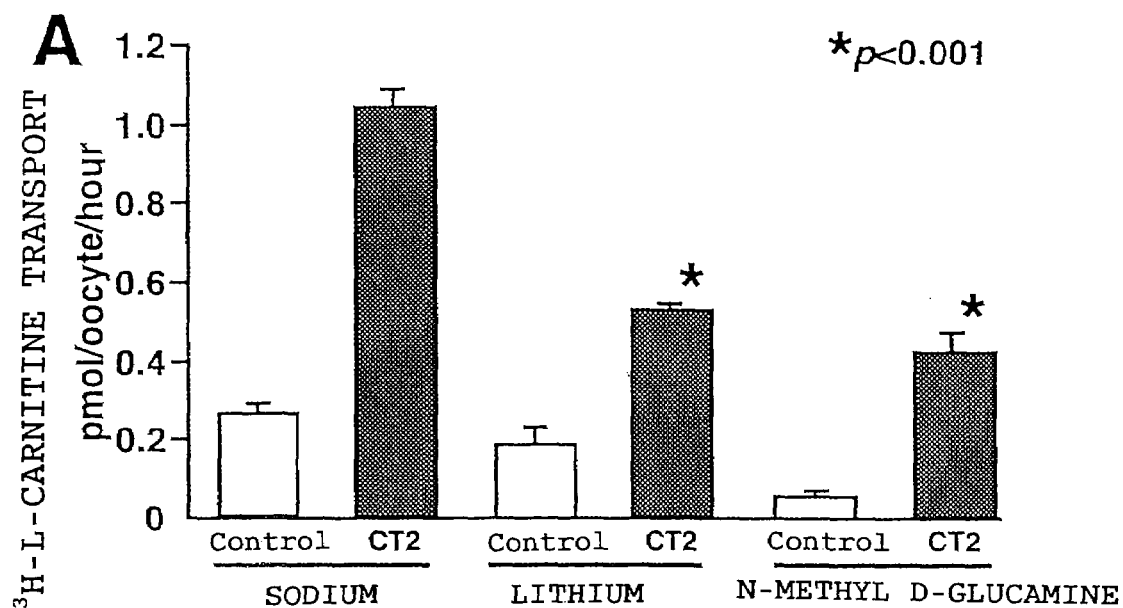
FIG. 3 shows (A) a result of influences of added salts and (B) a result of influences of pH of an experiment on carnitine uptake by oocytes into which the cRNA of human CT2 gene was injected.
Figure 3:
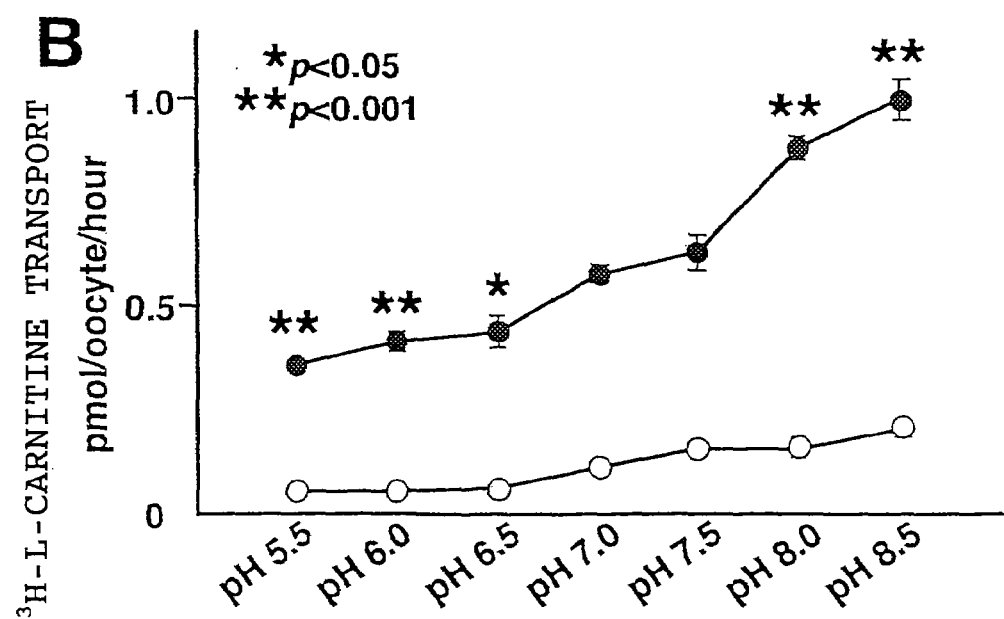

When extracellular sodium is substituted with lithium and N-methyl-D-glucamine, the carnitine transport by CT2 was decreased to reveal that the CT2 is an extracellular sodium dependent carnitine transporter (FIG. 3A). However, the uptake was not perfectly decreased when the extracellular sodium was substituted with lithium and N-methyl-D-glucamine, thereby it was revealed that CT2 is dependent on a partial extracellular sodium.

(5) A pH dependence of the CT2 in the carnitine transport was studied.

As shown in FIG. 3B, when an extracellular pH was inclined to acidity, the carnitine transport by CT2 was decreased.

(6) In order to study further on the substrate selectivity of CT2, in the $^3$H-carnitine uptake experiment system by oocytes into which CT2cRNA was injected, various carnitine analogs were added to the system and its influences were investigated (inhibition experiment).

Figure 4:
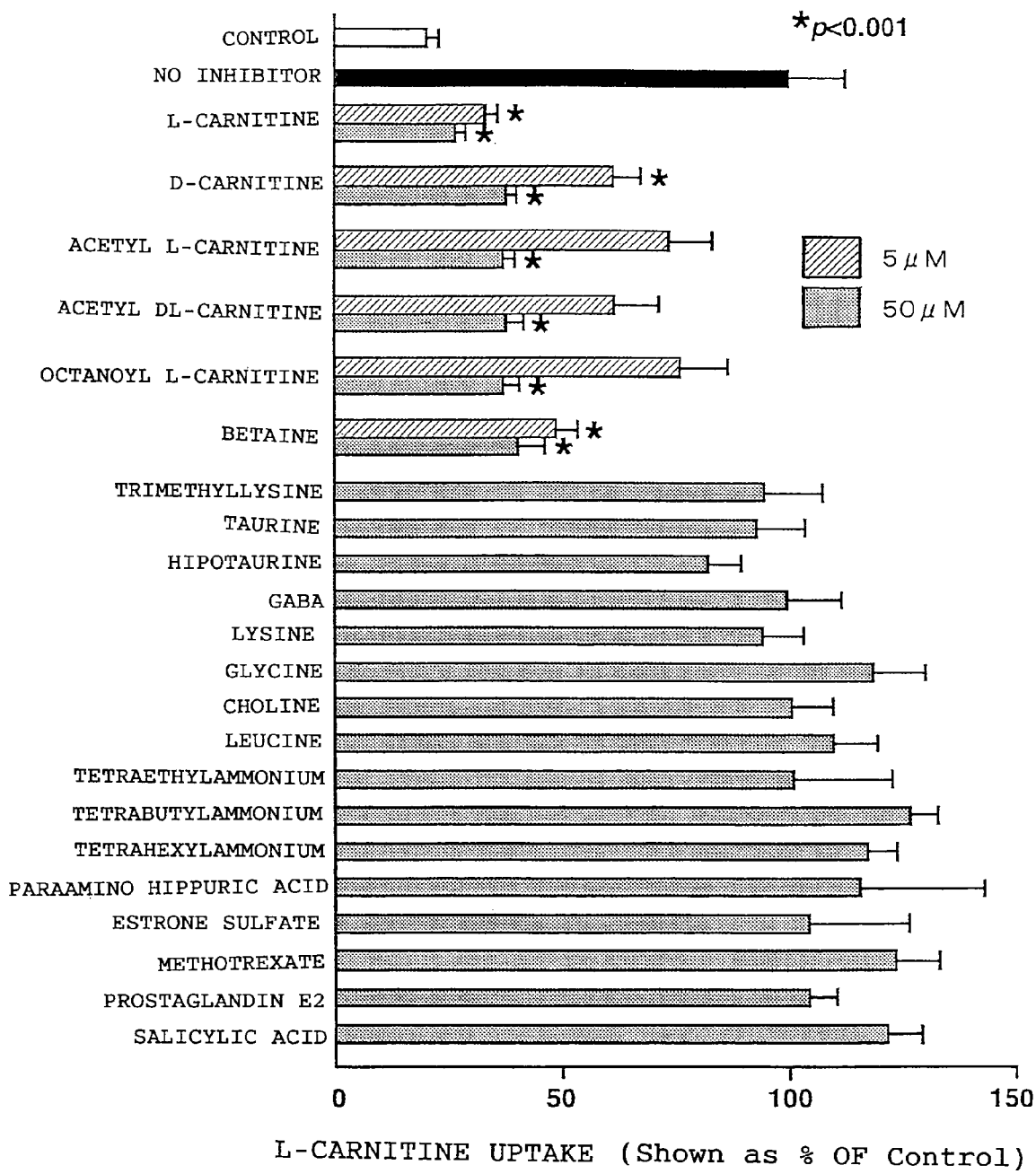
FIG. 4 shows a result of influence of additions of carnitine analogs to a system of an experiment on carnitine uptake by oocytes into which the cRNA of human CT2 gene was injected.

The $^3$H-carnitine uptake experiment was performed in accordance with the above-described method using oocytes into which CT2cRNA was injected. 50 nM $^3$H-carnitine uptake was measured in the presence or absence of 5 μM or 50 μM of various compounds (unlabelled). As a result, various carnitine analogs (D-carnitine, acetyl L-carnitine, acetyl DL-carnitine, octanoyl L-carnitine, betaine and the like) significantly inhibited the $^3$H-carnitine transport by CT2 (FIG. 4). On the other hand, anionic substances and cationic substances such as paraamino hippuric acid and tetraethylammnonium did not show inhibition effect (FIG. 4). From the above results, it was revealed that the CT2 is a specific transporter of carnitine and carnitine analogs.

(7) Expressions of CT2 gene in human tissues (northern blotting) were analyzed.

Figure 5:
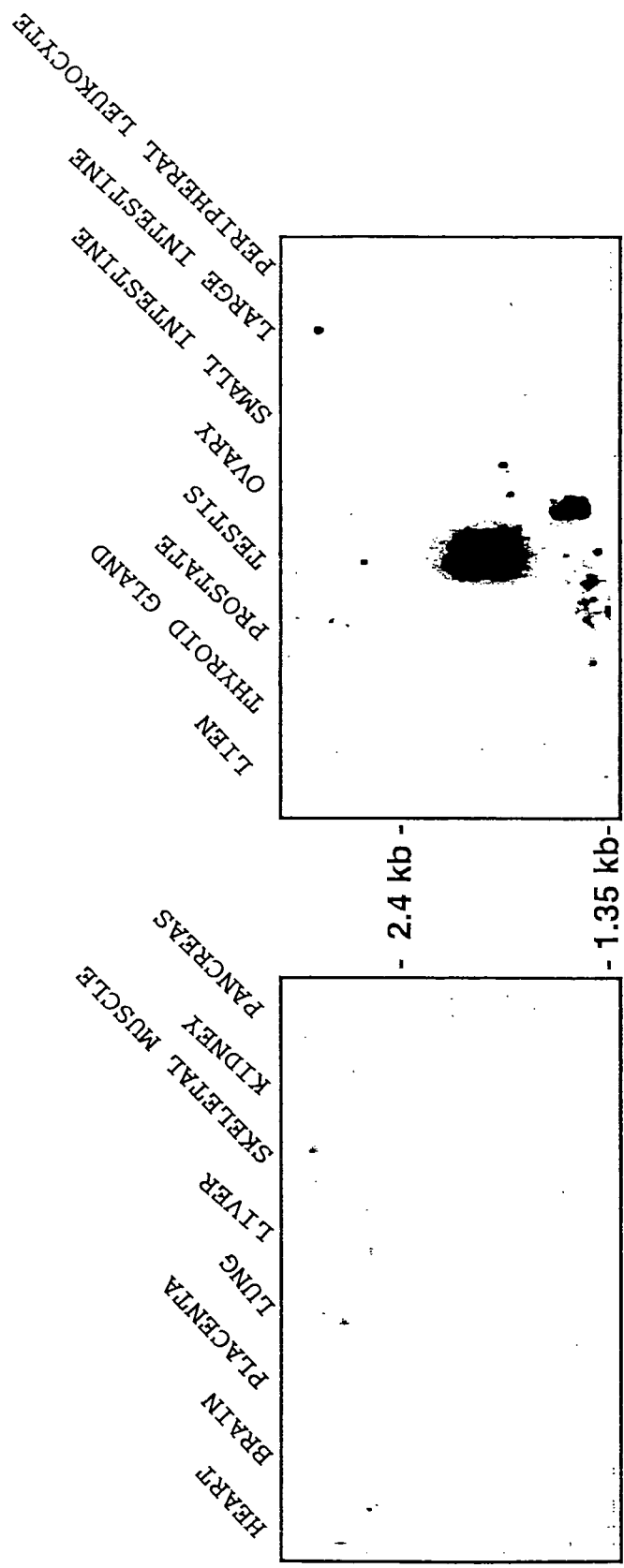
FIG. 5 is a photo substituted for drawing, showing a result of analyses of CT2 gene mRNA expressions in the human organs by the northern blotting method.

The full length of the CT2cDNA was labeled with $^{32}$P-dCTP, and using it as a probe, hybridization of a filter (product of Clontech) blotted RNAs extracted from various human tissues was conducted. The hybridization was conducted overnight in a hybridization solution in which the full length of the CT2cDNA was contained, and then the filter was washed with 0.1×SSC containing 0.1% SDS at 65° C. As a result of the northern blotting (FIG. 5), a strong band was detected only in the testis.

(8) An immunological study on a protein encoded by the CT2 gene in the testis and the epididymis was conducted.

Figure 6:
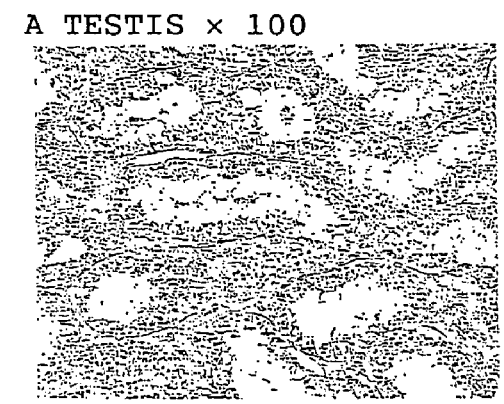
FIGS. 6A-6F show the results of immunohistological analyses of CT2 protein expression in the testis and the epididymis, an experiment described in Example 1 (8)
Figure 6:
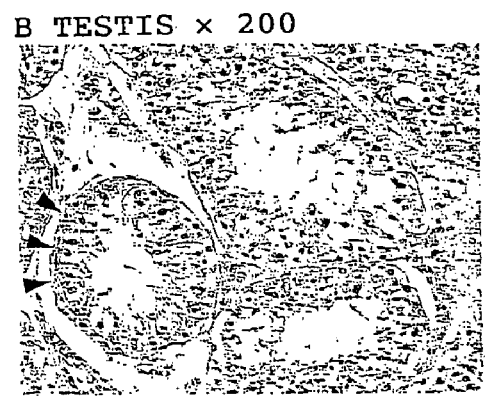
Figure 6:
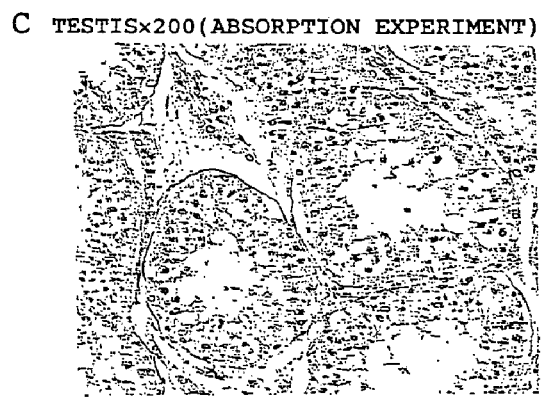
Figure 6:
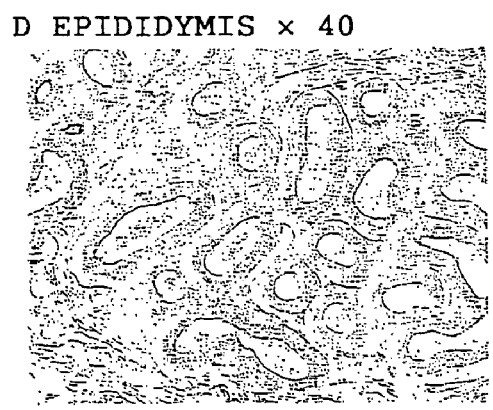
Figure 6:
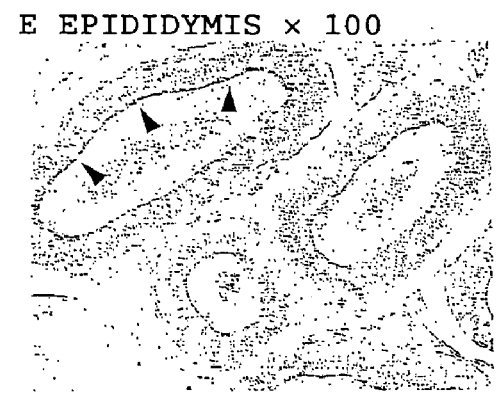
Figure 6:
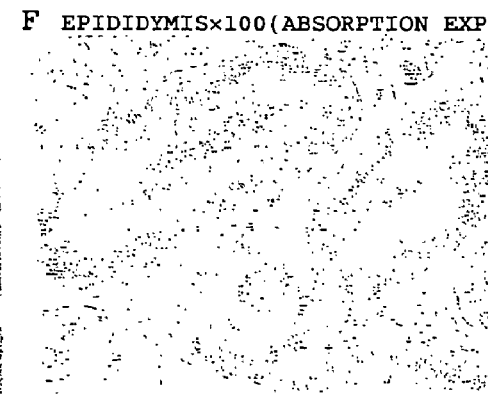

A polypeptide comprising 14 amino acid residues of a carboxyl terminal of the CT2 protein was synthesized, and it was immunized a rabbit to obtain an antiserum. A paraffin section of the human testis was subjected to a deparaffinization and then treated with 3% hydrogen peroxide solution to inactivate endogenous peroxidase. The section was incubated with an affinity purified polyclonal anti-CT2 antibody (primary antibody) for 24 hours, and then reacted with anti-rabbit IgG antibody labeled with peroxidase. Finally, by adding diaminobenzidine, which is a substrate for peroxidase, sites in which brown precipitation was obtained were observed with an optical microscope. As shown in FIG. 6, significant stains were observed in a cytoplasm of a Sertoli cell of the testis and a luminal side of an epithelial cell of the epididymis (an arrow in FIG. 6 indicates the CT2 expression site). Accordingly, the CT2 is a transporter which provides carnitine in Sertoli cells of the testis and transports carnitine from blood to the lumens of the epididymis.

(9) A structure of the CT2 gene in a human genome was analyzed.

Publicly disclosed information of human genome analysis results was searched by using a homology search program to find an exon-intron structure of the CT2 gene. As shown in FIG. 7, the CT2 gene is constituted of 10 exons, and a starting codon exists in the second exon.

INDUSTRIAL APPLICABILITY

The carnitine transporter specific to the testis and the epididymis selectively transporting carnitine and a gene thereof of the present invention enable an in vitro study on transport of carnitine and its analog at an expression site of the said transporter as well as a prediction of kinetics of the compounds in the genital organ based on the study. Carnitine is the essential factor for producing energy required for mobility and fertilizability of the sperms, and it is considered that the invention of the said transporter will contribute to clarification of the cause of the idiopathic male infertility in future. Further, by clarifying a control factor modulating the expression of the said transporter, the invention can be applied to developments of a method of modulating the ability of transporting carnitine and a method of modulating the sperm fertilizability.

The invention claimed is:

1. A method for screening a compound which inhibits or enhances the carnitine transporting activity of the protein consisting of SEQ ID NO: 2, the method comprising a) providing a cell having the functional protein consisting of SEQ ID NO: 2, b) contacting the cell with carnitine, c) incubating the cell with the compound to be screened and d) detecting the carnitine transporting activity of the protein consisting of SEQ ID NO: 2 of the cell, wherein an inhibition or enhancement in the carnitine transporting activity of the protein identifies the compound being screened.

* * * * *